(12) United States Patent
Mathieu et al.

(10) Patent No.: US 9,572,681 B2
(45) Date of Patent: *Feb. 21, 2017

(54) INTERVERTEBRAL IMPLANT

(75) Inventors: Claude Mathieu, Zurich (CH);
Christopher Marden John Cain, Eastwood (AU)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/284,747

(22) Filed: Oct. 28, 2011

(65) Prior Publication Data

US 2012/0109311 A1 May 3, 2012

Related U.S. Application Data

(63) Continuation of application No. 13/012,626, filed on Jan. 24, 2011, which is a continuation of application No. 12/574,222, filed on Oct. 6, 2009, now Pat. No. 7,875,076, which is a continuation of application No. 11/751,757, filed on May 22, 2007, now Pat. No. 7,618,456, which is a continuation of application No. 10/923,534, filed on Aug. 19, 2004, now Pat. No. 7,232,464, which is a continuation of application No. PCT/CH02/00099, filed on Feb. 19, 2002.

(51) Int. Cl.
*A61F 2/44* (2006.01)
*A61B 17/80* (2006.01)
*A61B 17/86* (2006.01)
*A61F 2/30* (2006.01)

(52) U.S. Cl.
CPC ......... *A61F 2/4465* (2013.01); *A61B 17/8052* (2013.01); *A61F 2/442* (2013.01); *A61B 17/86* (2013.01); *A61F 2/4455* (2013.01); *A61F 2002/30004* (2013.01); *A61F 2002/30774* (2013.01); *A61F 2002/30777* (2013.01); *A61F 2002/30794* (2013.01); *A61F 2002/30841* (2013.01); *A61F 2002/4475* (2013.01); *A61F 2250/0014* (2013.01); *A61F 2310/00011* (2013.01)

(58) Field of Classification Search
CPC .................................. A61F 2/44; A61F 2/4455
USPC .............................................. 623/17.11–17.16
See application file for complete search history.

(56) References Cited

U.S. PATENT DOCUMENTS

| | | |
|---|---|---|
| 424,836 A | 4/1890 | Thompson |
| 1,105,105 A | 7/1914 | Sherman |
| 1,200,797 A | 10/1916 | Barbe |
| 2,151,919 A | 3/1939 | Jacobson |
| 2,372,888 A | 4/1945 | Edward |

(Continued)

FOREIGN PATENT DOCUMENTS

| | | |
|---|---|---|
| AU | 2004/232317 | 11/2010 |
| CA | 2317791 | 8/1999 |

(Continued)

OTHER PUBLICATIONS

U.S. Appl. No. 11/199,599: Preliminary Amendment dated Jan. 9, 2008, 2 pages.

(Continued)

*Primary Examiner* — Bruce E Snow
(74) *Attorney, Agent, or Firm* — Baker & Hostetler LLP

(57) ABSTRACT

The intervertebral three-dimensional structure comprises a top side, an underside, a front face, a rear face, and a plurality of boreholes designed to receive affixation elements.

9 Claims, 3 Drawing Sheets

(56) References Cited

U.S. PATENT DOCUMENTS

| | | |
|---|---|---|
| 2,621,145 A | 12/1952 | Sano |
| 2,782,827 A | 2/1957 | Joseph |
| 2,906,311 A | 9/1959 | Boyd |
| 2,972,367 A | 2/1961 | Wootton |
| 3,062,253 A | 11/1962 | Melvin |
| 3,272,249 A | 9/1966 | Houston |
| 3,350,103 A | 10/1967 | Ahlstone |
| 3,426,364 A | 2/1969 | Lumb et al. |
| 3,561,075 A | 2/1971 | Selinko |
| 3,579,831 A | 5/1971 | Stevens et al. |
| 3,707,303 A | 12/1972 | Petri |
| 3,810,703 A | 5/1974 | Pasbrig |
| 3,867,728 A | 2/1975 | Stubstad et al. |
| 3,899,897 A | 8/1975 | Boerger et al. |
| 3,945,671 A | 3/1976 | Gerlach |
| 4,017,946 A | 4/1977 | Soja |
| 4,056,301 A | 11/1977 | Norden |
| 4,123,132 A | 10/1978 | Hardy |
| 4,135,506 A | 1/1979 | Ulrich |
| 4,278,120 A | 7/1981 | Hart et al. |
| 4,280,875 A | 7/1981 | Werres |
| 4,285,377 A | 8/1981 | Hart |
| 4,288,902 A | 9/1981 | Franz |
| 4,297,063 A | 10/1981 | Hart |
| 4,298,993 A | 11/1981 | Kovaleva et al. |
| 4,299,902 A | 11/1981 | Soma et al. |
| 4,349,921 A | 9/1982 | Kuntz |
| 4,388,921 A | 6/1983 | Sutter et al. |
| 4,394,370 A | 7/1983 | Jefferies |
| 4,450,591 A | 5/1984 | Rappaport |
| 4,484,570 A | 11/1984 | Sutter et al. |
| 4,488,543 A | 12/1984 | Tornier |
| 4,501,269 A | 2/1985 | Bagby |
| 4,503,848 A | 3/1985 | Caspar et al. |
| 4,512,038 A | 4/1985 | Alexander et al. |
| 4,545,374 A | 10/1985 | Jacobson |
| 4,553,890 A | 11/1985 | Gulistan |
| 4,599,086 A | 7/1986 | Doty |
| 4,627,853 A | 12/1986 | Campbell et al. |
| 4,640,524 A | 2/1987 | Sedlmair |
| 4,648,768 A | 3/1987 | Hambric |
| 4,678,470 A | 7/1987 | Nashef et al. |
| 4,708,377 A | 11/1987 | Hunting |
| 4,711,760 A | 12/1987 | Blaushild |
| 4,714,469 A | 12/1987 | Kenna |
| 4,717,115 A | 1/1988 | Schmitz et al. |
| 4,743,256 A | 5/1988 | Brantigan |
| 4,781,721 A | 11/1988 | Grundei |
| 4,793,335 A | 12/1988 | Frey et al. |
| 4,804,290 A | 2/1989 | Balsells |
| 4,812,094 A | 3/1989 | Grube |
| 4,829,152 A | 5/1989 | Rostoker et al. |
| 4,834,757 A | 5/1989 | Brantigan |
| 4,858,603 A | 8/1989 | Clemow et al. |
| 4,872,452 A | 10/1989 | Alexson |
| 4,878,915 A | 11/1989 | Brantigan |
| 4,904,261 A | 2/1990 | Dove et al. |
| 4,917,704 A | 4/1990 | Frey et al. |
| 4,936,851 A | 6/1990 | Fox et al. |
| 4,950,296 A | 8/1990 | McIntyre |
| 4,955,908 A | 9/1990 | Frey et al. |
| 4,961,740 A | 10/1990 | Ray et al. |
| 4,976,576 A | 12/1990 | Mahaney |
| 4,978,350 A | 12/1990 | Wagenknecht |
| 4,994,084 A | 2/1991 | Brennan |
| 4,997,432 A | 3/1991 | Keller |
| 5,006,120 A | 4/1991 | Carter |
| 5,010,783 A | 4/1991 | Sparks et al. |
| 5,017,069 A | 5/1991 | Stencel |
| 5,020,949 A | 6/1991 | Davidson et al. |
| 5,026,373 A | 6/1991 | Ray et al. |
| 5,030,220 A | 7/1991 | Howland |
| 5,047,058 A | 9/1991 | Roberts et al. |
| 5,053,049 A | 10/1991 | Campbell |
| 5,062,850 A | 11/1991 | MacMillan et al. |
| 5,071,437 A | 12/1991 | Steffee |
| 5,084,051 A | 1/1992 | Tormala et al. |
| 5,085,660 A | 2/1992 | Lin |
| 5,096,150 A | 3/1992 | Westwood |
| 5,108,438 A | 4/1992 | Stone et al. |
| 5,112,354 A | 5/1992 | Sires |
| 5,116,374 A | 5/1992 | Stone |
| 5,118,235 A | 6/1992 | Dill |
| 5,139,424 A | 8/1992 | Yli-Urpo |
| 5,147,404 A | 9/1992 | Downey |
| 5,180,381 A | 1/1993 | Aust et al. |
| 5,192,327 A | 3/1993 | Brantigan |
| 5,201,736 A | 4/1993 | Strauss |
| 5,207,543 A | 5/1993 | Kirma |
| 5,211,664 A | 5/1993 | Tepic et al. |
| 5,235,034 A | 8/1993 | Bobsein et al. |
| 5,238,342 A | 8/1993 | Stencel |
| 5,258,031 A | 11/1993 | Salib et al. |
| 5,275,601 A | 1/1994 | Gogolewski et al. |
| 5,281,226 A | 1/1994 | Davydov et al. |
| 5,282,861 A | 2/1994 | Kaplan |
| 5,284,655 A | 2/1994 | Bogdansky et al. |
| 5,290,312 A | 3/1994 | Kojimoto et al. |
| 5,298,254 A | 3/1994 | Prewett et al. |
| 5,304,021 A | 4/1994 | Oliver et al. |
| 5,306,308 A | 4/1994 | Gross et al. |
| 5,306,309 A | 4/1994 | Wagner et al. |
| 5,314,476 A | 5/1994 | Prewett et al. |
| 5,314,477 A | 5/1994 | Marnay |
| 5,330,535 A | 7/1994 | Moser et al. |
| 5,348,788 A | 9/1994 | White |
| 5,368,593 A | 11/1994 | Stark |
| 5,380,323 A | 1/1995 | Howland |
| 5,385,583 A | 1/1995 | Cotrel |
| 5,397,364 A | 3/1995 | Kozak et al. |
| 5,405,391 A | 4/1995 | Hednerson et al. |
| 5,411,348 A | 5/1995 | Balsells |
| 5,423,817 A | 6/1995 | Lin |
| 5,425,772 A | 6/1995 | Brantigan |
| 5,431,658 A | 7/1995 | Moskovich |
| 5,439,684 A | 8/1995 | Prewett et al. |
| 5,443,514 A | 8/1995 | Steffee |
| 5,443,515 A | 8/1995 | Cohen et al. |
| 5,458,638 A | 10/1995 | Kuslich et al. |
| 5,458,641 A | 10/1995 | Ramirez |
| 5,458,643 A | 10/1995 | Oka et al. |
| 5,478,342 A | 12/1995 | Kohrs |
| 5,484,437 A | 1/1996 | Michelson |
| 5,487,744 A | 1/1996 | Howland |
| 5,489,308 A | 2/1996 | Kuslich et al. |
| 5,507,818 A | 4/1996 | McLaughlin |
| 5,514,180 A | 5/1996 | Heggeness et al. |
| 5,520,690 A | 5/1996 | Errico et al. |
| 5,522,899 A | 6/1996 | Michelson |
| 5,531,746 A | 7/1996 | Errico et al. |
| 5,534,030 A | 7/1996 | Navarro et al. |
| 5,534,031 A | 7/1996 | Matsuzaki et al. |
| 5,534,032 A | 7/1996 | Hodorek |
| 5,545,842 A | 8/1996 | Balsells |
| 5,549,612 A | 8/1996 | Yapp et al. |
| 5,549,679 A | 8/1996 | Kuslich |
| 5,550,172 A | 8/1996 | Regula et al. |
| 5,554,191 A | 9/1996 | Lahille et al. |
| 5,556,430 A | 9/1996 | Gendler |
| 5,556,431 A | 9/1996 | Buttner-Janz |
| 5,569,308 A | 10/1996 | Sottosanti |
| 5,570,983 A | 11/1996 | Hollander |
| 5,571,190 A | 11/1996 | Ulrich et al. |
| 5,571,192 A | 11/1996 | Schonhoffer |
| 5,578,034 A | 11/1996 | Estes |
| 5,593,409 A | 1/1997 | Michelson |
| 5,597,278 A | 1/1997 | Peterkort |
| 5,601,553 A | 2/1997 | Trebing et al. |
| 5,601,554 A | 2/1997 | Howland et al. |
| 5,607,428 A | 3/1997 | Lin |
| 5,607,474 A | 3/1997 | Athanasiou et al. |
| 5,609,635 A | 3/1997 | Michelson |
| 5,609,636 A | 3/1997 | Kohrs et al. |
| 5,609,637 A | 3/1997 | Biedermann et al. |

(56) References Cited

U.S. PATENT DOCUMENTS

| | | |
|---|---|---|
| 5,616,144 A | 4/1997 | Yapp et al. |
| 5,620,448 A | 4/1997 | Puddu |
| 5,642,960 A | 7/1997 | Salice |
| 5,645,596 A | 7/1997 | Kim et al. |
| 5,645,606 A | 7/1997 | Oehy et al. |
| 5,653,708 A | 8/1997 | Howland |
| 5,669,909 A | 9/1997 | Zdeblick et al. |
| 5,674,296 A | 10/1997 | Bryan et al. |
| 5,676,666 A | 10/1997 | Oxland |
| 5,676,699 A | 10/1997 | Gogolewski |
| 5,681,311 A | 10/1997 | Foley et al. |
| 5,683,216 A | 11/1997 | Erbes |
| 5,683,394 A | 11/1997 | Rinner |
| 5,683,463 A | 11/1997 | Godefroy et al. |
| 5,702,449 A | 12/1997 | McKay |
| 5,702,451 A | 12/1997 | Biedermann et al. |
| 5,702,453 A | 12/1997 | Rabbe et al. |
| 5,702,455 A | 12/1997 | Saggar |
| 5,713,899 A | 2/1998 | Marnay et al. |
| 5,713,900 A | 2/1998 | Benzel et al. |
| 5,725,531 A | 3/1998 | Shapiro |
| 5,725,588 A | 3/1998 | Errico et al. |
| 5,728,159 A | 3/1998 | Stroever et al. |
| 5,735,853 A | 4/1998 | Olerud |
| 5,735,905 A | 4/1998 | Parr |
| 5,755,796 A | 5/1998 | Ibo et al. |
| 5,755,798 A | 5/1998 | Papavero et al. |
| 5,766,251 A | 6/1998 | Koshino |
| 5,766,252 A | 6/1998 | Henry et al. |
| 5,766,253 A | 6/1998 | Brosnahan, III |
| 5,772,661 A | 6/1998 | Michelson |
| 5,776,194 A | 7/1998 | Mikol et al. |
| 5,776,196 A | 7/1998 | Matsuzaki et al. |
| 5,776,197 A | 7/1998 | Rabbe et al. |
| 5,776,198 A | 7/1998 | Rabbe et al. |
| 5,776,199 A | 7/1998 | Michelson |
| 5,778,804 A | 7/1998 | Read |
| 5,782,915 A | 7/1998 | Stone |
| 5,782,919 A | 7/1998 | Zdeblick et al. |
| 5,785,710 A | 7/1998 | Michelson |
| 5,800,433 A | 9/1998 | Benzel et al. |
| 5,836,948 A | 11/1998 | Zucherman et al. |
| 5,860,973 A | 1/1999 | Michelson |
| 5,861,041 A | 1/1999 | Tienboon |
| 5,865,845 A | 2/1999 | Thalgott |
| 5,865,849 A | 2/1999 | Stone |
| 5,876,402 A | 3/1999 | Errico et al. |
| 5,876,452 A | 3/1999 | Athanasiou et al. |
| 5,879,389 A | 3/1999 | Koshino |
| 5,885,299 A | 3/1999 | Winslow et al. |
| 5,888,222 A | 3/1999 | Coates et al. |
| 5,888,223 A | 3/1999 | Bray, Jr. |
| 5,888,224 A | 3/1999 | Beckers et al. |
| 5,888,227 A | 3/1999 | Cottle |
| 5,895,426 A | 4/1999 | Scarborough et al. |
| 5,899,939 A | 5/1999 | Boyce et al. |
| 5,902,303 A | 5/1999 | Eckhof et al. |
| 5,902,338 A | 5/1999 | Stone |
| 5,904,683 A | 5/1999 | Pohndorf et al. |
| 5,904,719 A | 5/1999 | Errico et al. |
| 5,906,616 A | 5/1999 | Pavlov et al. |
| 5,910,315 A | 6/1999 | Stevenson et al. |
| 5,911,758 A | 6/1999 | Oehy et al. |
| 5,920,312 A | 7/1999 | Wagner et al. |
| 5,922,027 A | 7/1999 | Stone |
| 5,931,838 A | 8/1999 | Vito |
| 5,944,755 A | 8/1999 | Stone |
| 5,951,558 A | 9/1999 | Fiz |
| 5,954,722 A | 9/1999 | Bono |
| 5,958,314 A | 9/1999 | Draenet |
| 5,964,807 A | 10/1999 | Gan et al. |
| 5,968,098 A | 10/1999 | Winslow |
| 5,972,368 A | 10/1999 | McKay |
| 5,976,141 A | 11/1999 | Haag et al. |
| 5,976,187 A | 11/1999 | Richelsoph |
| 5,980,522 A | 11/1999 | Koros et al. |
| 5,981,828 A | 11/1999 | Nelson et al. |
| 5,984,967 A | 11/1999 | Zdeblick et al. |
| 5,989,289 A | 11/1999 | Coates et al. |
| 6,001,099 A | 12/1999 | Huebner |
| 6,008,433 A | 12/1999 | Stone |
| 6,013,853 A | 1/2000 | Athanasiou et al. |
| 6,017,345 A | 1/2000 | Richelsoph |
| 6,025,538 A | 2/2000 | Yaccarino, III |
| 6,033,405 A | 3/2000 | Winslow et al. |
| 6,033,438 A | 3/2000 | Bianchi et al. |
| 6,039,762 A | 3/2000 | McKay |
| 6,045,579 A | 4/2000 | Hochshuler et al. |
| 6,045,580 A | 4/2000 | Scarborough et al. |
| 6,056,749 A | 5/2000 | Kuslich |
| 6,066,175 A | 5/2000 | Henderson et al. |
| 6,080,158 A | 6/2000 | Lin |
| 6,080,193 A | 6/2000 | Hochshuler et al. |
| 6,086,593 A | 7/2000 | Bonutti |
| 6,086,614 A | 7/2000 | Mumme |
| 6,090,998 A | 7/2000 | Grooms et al. |
| 6,096,080 A | 8/2000 | Nicholson et al. |
| 6,096,081 A | 8/2000 | Grivas et al. |
| 6,099,531 A | 8/2000 | Bonutti |
| 6,110,482 A | 8/2000 | Khouri et al. |
| 6,113,637 A | 9/2000 | Gill et al. |
| 6,113,638 A | 9/2000 | Williams et al. |
| 6,120,503 A | 9/2000 | Michelson |
| 6,123,731 A | 9/2000 | Boyce et al. |
| 6,129,763 A | 10/2000 | Chauvin et al. |
| 6,136,001 A | 10/2000 | Michelson |
| 6,139,550 A | 10/2000 | Michelson |
| 6,143,030 A | 11/2000 | Schroder |
| 6,143,033 A | 11/2000 | Paul et al. |
| 6,146,421 A | 11/2000 | Gordon et al. |
| 6,156,070 A | 12/2000 | Incavo et al. |
| 6,193,721 B1 | 2/2001 | Michelson |
| 6,193,756 B1 | 2/2001 | Studer et al. |
| 6,193,757 B1 | 2/2001 | Foley et al. |
| 6,200,347 B1 | 3/2001 | Anderson et al. |
| 6,206,922 B1 | 3/2001 | Zdeblick et al. |
| 6,224,602 B1 | 5/2001 | Hayes |
| 6,231,610 B1 | 5/2001 | Geisler |
| 6,235,033 B1 | 5/2001 | Brace et al. |
| 6,235,034 B1 | 5/2001 | Bray |
| 6,235,059 B1 | 5/2001 | Benezech et al. |
| 6,241,731 B1 | 6/2001 | Fiz |
| 6,241,769 B1 | 6/2001 | Nicholson et al. |
| 6,245,108 B1 | 6/2001 | Biscup |
| 6,258,089 B1 | 7/2001 | Campbell et al. |
| 6,258,125 B1 | 7/2001 | Paul et al. |
| 6,261,291 B1 | 7/2001 | Talaber et al. |
| 6,261,586 B1 | 7/2001 | McKay |
| 6,264,695 B1 | 7/2001 | Stoy |
| 6,270,528 B1 | 8/2001 | McKay |
| 6,306,139 B1 | 10/2001 | Fuentes |
| 6,322,562 B1 | 11/2001 | Wolter |
| 6,331,179 B1 | 12/2001 | Freid et al. |
| 6,342,074 B1 | 1/2002 | Simpson |
| 6,364,880 B1 | 4/2002 | Michelson |
| 6,371,986 B1 | 4/2002 | Bagby |
| 6,371,988 B1 | 4/2002 | Pafford et al. |
| 6,371,989 B1 | 4/2002 | Chauvin et al. |
| 6,375,681 B1 | 4/2002 | Truscott |
| 6,383,186 B1 | 5/2002 | Michelson |
| 6,387,130 B1 | 5/2002 | Stone et al. |
| 6,395,031 B1 | 5/2002 | Foley et al. |
| 6,398,811 B1 | 6/2002 | McKay |
| 6,413,259 B1 | 7/2002 | Lyons et al. |
| 6,423,063 B1 | 7/2002 | Bonutti |
| 6,432,106 B1 | 8/2002 | Fraser |
| 6,443,987 B1 | 9/2002 | Bryan |
| 6,447,512 B1 | 9/2002 | Landry et al. |
| 6,447,546 B1 | 9/2002 | Bramlet et al. |
| 6,454,771 B1 | 9/2002 | Michelson |
| 6,458,158 B1 | 10/2002 | Anderson et al. |
| 6,461,359 B1 | 10/2002 | Tribus et al. |
| 6,468,311 B2 | 10/2002 | Boyd et al. |
| 6,471,724 B2 | 10/2002 | Zdeblick et al. |

(56) References Cited

U.S. PATENT DOCUMENTS

| | | |
|---|---|---|
| 6,482,233 B1 | 11/2002 | Aebi et al. |
| 6,503,250 B2 | 1/2003 | Paul |
| 6,511,509 B1 | 1/2003 | Ford et al. |
| 6,524,312 B2 | 2/2003 | Landry et al. |
| 6,558,387 B2 | 5/2003 | Errico et al. |
| 6,558,423 B1 | 5/2003 | Michelson |
| 6,558,424 B2 | 5/2003 | Thalgott |
| 6,562,073 B2 | 5/2003 | Foley |
| 6,569,201 B2 | 5/2003 | Moumene et al. |
| 6,575,975 B2 | 6/2003 | Brace et al. |
| 6,576,017 B2 | 6/2003 | Foley et al. |
| 6,579,290 B1 | 6/2003 | Hardcastle et al. |
| 6,592,624 B1 | 7/2003 | Fraser et al. |
| 6,602,291 B1 | 8/2003 | Ray et al. |
| 6,605,090 B1 | 8/2003 | Trieu et al. |
| 6,616,671 B2 | 9/2003 | Landry et al. |
| 6,620,163 B1 | 9/2003 | Michelson |
| 6,623,486 B1 | 9/2003 | Weaver et al. |
| 6,629,998 B1 | 10/2003 | Lin |
| 6,638,310 B2 | 10/2003 | Lin et al. |
| 6,645,212 B2 | 11/2003 | Goldhahn et al. |
| 6,652,525 B1 | 11/2003 | Assaker et al. |
| 6,656,181 B2 | 12/2003 | Dixon et al. |
| 6,679,887 B2 | 1/2004 | Nicholson et al. |
| 6,682,561 B2 | 1/2004 | Songer et al. |
| 6,682,563 B2 | 1/2004 | Scharf |
| 6,695,846 B2 | 2/2004 | Richelsoph et al. |
| 6,695,851 B2 | 2/2004 | Zdeblick et al. |
| 6,706,067 B2 | 3/2004 | Shimp et al. |
| 6,709,456 B2 | 3/2004 | Langberg et al. |
| 6,712,818 B1 | 3/2004 | Michelson |
| 6,730,127 B2 | 5/2004 | Michelson |
| 6,736,850 B2 | 5/2004 | Davis |
| 6,761,739 B2 | 7/2004 | Shepard |
| 6,770,096 B2 | 8/2004 | Bolger et al. |
| 6,786,909 B1 | 9/2004 | Dransfeld et al. |
| 6,800,092 B1 | 10/2004 | Williams et al. |
| 6,805,714 B2 | 10/2004 | Sutcliffe |
| 6,808,537 B2 | 10/2004 | Michelson |
| 6,824,564 B2 | 11/2004 | Crozet |
| 6,833,006 B2 | 12/2004 | Foley et al. |
| 6,837,905 B1 | 1/2005 | Lieberman |
| 6,849,093 B2 | 2/2005 | Michelson |
| 6,855,168 B2 | 2/2005 | Crozet |
| 6,863,673 B2 | 3/2005 | Gerbec et al. |
| 6,872,915 B2 | 3/2005 | Koga et al. |
| 6,884,242 B2 | 4/2005 | LeHuec et al. |
| 6,890,334 B2 | 5/2005 | Brace et al. |
| 6,896,701 B2 | 5/2005 | Boyd et al. |
| 6,899,735 B2 | 5/2005 | Coates et al. |
| 6,902,578 B1 | 6/2005 | Anderson et al. |
| 6,916,320 B2 | 7/2005 | Michelson |
| 6,923,756 B2 | 8/2005 | Sudakov et al. |
| 6,953,477 B2 | 10/2005 | Berry |
| 6,962,606 B2 | 11/2005 | Michelson |
| 6,964,664 B2 | 11/2005 | Freid et al. |
| 6,964,687 B1 | 11/2005 | Bernard et al. |
| 6,972,019 B2 | 12/2005 | Michelson |
| 6,972,035 B2 | 12/2005 | Michelson |
| 6,974,479 B2 | 12/2005 | Trieu |
| 6,984,234 B2 | 1/2006 | Bray |
| 7,001,385 B2 | 2/2006 | Bonutti |
| 7,001,432 B2 | 2/2006 | Keller et al. |
| 7,018,416 B2 | 3/2006 | Hanson et al. |
| 7,033,394 B2 | 4/2006 | Michelson |
| 7,041,135 B2 | 5/2006 | Michelson |
| 7,044,968 B1 | 5/2006 | Yaccarino et al. |
| 7,044,972 B2 | 5/2006 | Mathys et al. |
| 7,048,765 B1 | 5/2006 | Grooms et al. |
| 7,060,097 B2 | 6/2006 | Fraser et al. |
| 7,066,961 B2 | 6/2006 | Michelson |
| 7,077,864 B2 | 7/2006 | Bryd, III et al. |
| 7,112,222 B2 | 9/2006 | Fraser et al. |
| 7,112,223 B2 | 9/2006 | Davis |
| 7,135,024 B2 | 11/2006 | Cook et al. |
| 7,135,043 B2 | 11/2006 | Nakahara et al. |
| 7,137,984 B2 | 11/2006 | Michelson |
| 7,147,665 B1 | 12/2006 | Bryan et al. |
| 7,163,561 B2 | 1/2007 | Michelson |
| 7,172,627 B2 | 2/2007 | Fiere et al. |
| 7,172,672 B2 | 2/2007 | Silverbrook |
| 7,226,452 B2 | 6/2007 | Zubok |
| 7,226,482 B2 | 6/2007 | Messerli et al. |
| 7,232,463 B2 | 6/2007 | Falahee |
| 7,232,464 B2 | 6/2007 | Mathieu et al. |
| 7,238,203 B2 | 7/2007 | Bagga et al. |
| 7,255,698 B2 | 8/2007 | Michelson |
| 7,276,082 B2 | 10/2007 | Zdeblick et al. |
| 7,320,708 B1 | 1/2008 | Bernstein |
| 7,323,011 B2 | 1/2008 | Shepard et al. |
| 7,442,209 B2 | 10/2008 | Michelson |
| 7,491,237 B2 | 2/2009 | Randall et al. |
| 7,534,265 B1 | 5/2009 | Boyd et al. |
| 7,594,932 B2 | 9/2009 | Aferzon et al. |
| 7,601,173 B2 | 10/2009 | Messerli et al. |
| 7,608,107 B2 | 10/2009 | Michelson |
| 7,618,456 B2 | 11/2009 | Mathieu et al. |
| 7,621,960 B2 | 11/2009 | Boyd et al. |
| 7,625,380 B2 | 12/2009 | Drewry et al. |
| 7,637,951 B2 | 12/2009 | Michelson |
| 7,655,042 B2 | 2/2010 | Foley et al. |
| 7,704,279 B2 | 4/2010 | Moskowitz et al. |
| 7,846,188 B2 | 12/2010 | Moskowitz et al. |
| 7,846,207 B2 | 12/2010 | Lechmann et al. |
| 7,862,616 B2 | 1/2011 | Lechmann et al. |
| 7,875,076 B2 | 1/2011 | Mathieu et al. |
| 7,942,903 B2 | 5/2011 | Moskowitz et al. |
| 7,993,403 B2 | 8/2011 | Foley et al. |
| 8,062,303 B2 | 11/2011 | Berry et al. |
| 8,128,700 B2 | 3/2012 | Delurio et al. |
| 8,182,532 B2 | 5/2012 | Anderson et al. |
| 8,211,148 B2 | 7/2012 | Zhang et al. |
| 8,273,127 B2 | 9/2012 | Jones et al. |
| 8,308,804 B2 | 11/2012 | Krueger |
| 8,328,872 B2 | 12/2012 | Duffield et al. |
| 8,343,222 B2 | 1/2013 | Cope |
| 8,353,913 B2 | 1/2013 | Moskowitz et al. |
| 8,382,768 B2 | 2/2013 | Berry et al. |
| 8,425,607 B2 | 4/2013 | Waugh et al. |
| 8,444,696 B2 | 5/2013 | Michelson |
| 8,465,546 B2 | 6/2013 | Jodaitis et al. |
| 8,540,774 B2 | 9/2013 | Kueenzi et al. |
| 8,545,567 B1 | 10/2013 | Kreuger |
| 8,641,743 B2 | 2/2014 | Michelson |
| 8,641,768 B2 | 2/2014 | Duffield et al. |
| 8,764,831 B2 | 7/2014 | Lechmann et al. |
| 9,005,295 B2 | 4/2015 | Kueenzi et al. |
| 2001/0001129 A1 | 5/2001 | McKay et al. |
| 2001/0005796 A1 | 6/2001 | Zdeblick et al. |
| 2001/0010021 A1 | 7/2001 | Boyd et al. |
| 2001/0016777 A1 | 8/2001 | Biscup |
| 2001/0020186 A1 | 9/2001 | Boyee et al. |
| 2001/0031254 A1 | 10/2001 | Bianchi et al. |
| 2001/0039456 A1 | 11/2001 | Boyer, II et al. |
| 2001/0041941 A1 | 11/2001 | Boyer, II et al. |
| 2002/0004683 A1 | 1/2002 | Michelson et al. |
| 2002/0010511 A1 | 1/2002 | Michelson |
| 2002/0016595 A1 | 2/2002 | Michelson |
| 2002/0022843 A1 | 2/2002 | Michelson |
| 2002/0029084 A1 | 3/2002 | Paul et al. |
| 2002/0065517 A1 | 5/2002 | Paul |
| 2002/0082597 A1 | 6/2002 | Fraser |
| 2002/0082603 A1 | 6/2002 | Dixon et al. |
| 2002/0091447 A1 | 7/2002 | Shimp et al. |
| 2002/0095155 A1 | 7/2002 | Michelson |
| 2002/0099376 A1 | 7/2002 | Michelson |
| 2002/0099378 A1 | 7/2002 | Michelson |
| 2002/0106393 A1 | 8/2002 | Bianchi et al. |
| 2002/0111680 A1 | 8/2002 | Michelson |
| 2002/0128712 A1 | 9/2002 | Michelson |
| 2002/0128717 A1 | 9/2002 | Alfaro et al. |
| 2002/0147450 A1 | 10/2002 | LeHuec et al. |
| 2002/0169508 A1 | 11/2002 | Songer et al. |
| 2002/0193880 A1 | 12/2002 | Fraser |

(56) References Cited

U.S. PATENT DOCUMENTS

| | | |
|---|---|---|
| 2003/0045939 A1 | 3/2003 | Casutt |
| 2003/0078666 A1 | 4/2003 | Ralph et al. |
| 2003/0078668 A1 | 4/2003 | Michelson |
| 2003/0125739 A1 | 7/2003 | Bagga et al. |
| 2003/0135277 A1 | 7/2003 | Bryan et al. |
| 2003/0153975 A1 | 8/2003 | Byrd et al. |
| 2003/0167092 A1 | 9/2003 | Foley |
| 2003/0195626 A1 | 10/2003 | Huppert |
| 2003/0195632 A1 | 10/2003 | Foley et al. |
| 2003/0199881 A1 | 10/2003 | Bonutti |
| 2003/0199983 A1 | 10/2003 | Michelson |
| 2004/0078078 A1 | 4/2004 | Shepard |
| 2004/0078081 A1 | 4/2004 | Ferree |
| 2004/0092929 A1 | 5/2004 | Zindrick |
| 2004/0093084 A1 | 5/2004 | Michelson |
| 2004/0102848 A1 | 5/2004 | Michelson |
| 2004/0126407 A1 | 7/2004 | Falahee |
| 2004/0133278 A1 | 7/2004 | Marino et al. |
| 2004/0143270 A1 | 7/2004 | Zucherman et al. |
| 2004/0176853 A1 | 9/2004 | Sennett et al. |
| 2004/0199254 A1 | 10/2004 | Louis et al. |
| 2004/0210219 A1 | 10/2004 | Bray |
| 2004/0210310 A1 | 10/2004 | Trieu |
| 2004/0210314 A1 | 10/2004 | Michelson |
| 2004/0249377 A1 | 12/2004 | Kaes et al. |
| 2004/0254644 A1 | 12/2004 | Taylor |
| 2005/0015149 A1 | 1/2005 | Michelson |
| 2005/0021143 A1 | 1/2005 | Keller |
| 2005/0033433 A1 | 2/2005 | Michelson |
| 2005/0049593 A1 | 3/2005 | Duong et al. |
| 2005/0049595 A1 | 3/2005 | Suh et al. |
| 2005/0065605 A1 | 3/2005 | Jackson |
| 2005/0065607 A1 | 3/2005 | Gross |
| 2005/0065608 A1 | 3/2005 | Michelson |
| 2005/0071008 A1 | 3/2005 | Kirschman |
| 2005/0085913 A1 | 4/2005 | Fraser et al. |
| 2005/0101960 A1 | 5/2005 | Fiere et al. |
| 2005/0149193 A1 | 7/2005 | Zucherman et al. |
| 2005/0154391 A1 | 7/2005 | Doherty et al. |
| 2005/0159813 A1 | 7/2005 | Molz |
| 2005/0159818 A1 | 7/2005 | Blain |
| 2005/0159819 A1 | 7/2005 | McCormick et al. |
| 2005/0171607 A1 | 8/2005 | Michelson |
| 2005/0177236 A1 | 8/2005 | Mathieu et al. |
| 2005/0240267 A1 | 10/2005 | Randall et al. |
| 2005/0240271 A1 | 10/2005 | Zubock et al. |
| 2005/0261767 A1 | 11/2005 | Anderson et al. |
| 2006/0020342 A1 | 1/2006 | Feree et al. |
| 2006/0030851 A1 | 2/2006 | Bray et al. |
| 2006/0079901 A1 | 4/2006 | Ryan et al. |
| 2006/0079961 A1 | 4/2006 | Michelson |
| 2006/0085071 A1 | 4/2006 | Lechmann et al. |
| 2006/0089717 A1 | 4/2006 | Krishna |
| 2006/0129240 A1 | 6/2006 | Lessar et al. |
| 2006/0136063 A1 | 6/2006 | Zeegers |
| 2006/0142765 A9 | 6/2006 | Dixon et al. |
| 2006/0195189 A1 | 8/2006 | Link et al. |
| 2006/0206208 A1 | 9/2006 | Michelson |
| 2006/0229725 A1 | 10/2006 | Lechmann et al. |
| 2007/0088441 A1 | 4/2007 | Duggal et al. |
| 2007/0093819 A1 | 4/2007 | Albert |
| 2007/0106384 A1 | 5/2007 | Bray et al. |
| 2007/0118125 A1 | 5/2007 | Orbay et al. |
| 2007/0123987 A1 | 5/2007 | Bernstein |
| 2007/0162130 A1 | 7/2007 | Rashbaum et al. |
| 2007/0168032 A1 | 7/2007 | Muhanna et al. |
| 2007/0219365 A1 | 9/2007 | Joyce et al. |
| 2007/0219635 A1 | 9/2007 | Mathieu et al. |
| 2007/0225806 A1 | 9/2007 | Squires et al. |
| 2007/0225812 A1 | 9/2007 | Gill |
| 2007/0250167 A1 | 10/2007 | Bray et al. |
| 2007/0270961 A1 | 11/2007 | Ferguson |
| 2008/0033440 A1 | 2/2008 | Moskowitz et al. |
| 2008/0051890 A1 | 2/2008 | Waugh et al. |
| 2008/0082169 A1 | 4/2008 | Gittings |
| 2008/0119933 A1 | 5/2008 | Aebi et al. |
| 2008/0133013 A1 | 6/2008 | Duggal et al. |
| 2008/0161925 A1 | 7/2008 | Brittan et al. |
| 2008/0177307 A1 | 7/2008 | Moskowitz et al. |
| 2008/0200984 A1 | 8/2008 | Jodaitis et al. |
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0269806 A1 | 10/2008 | Zhang et al. |
| 2008/0275455 A1 | 11/2008 | Berry et al. |
| 2008/0306596 A1 | 12/2008 | Jones et al. |
| 2009/0076608 A1 | 3/2009 | Gordon et al. |
| 2009/0105830 A1 | 4/2009 | Jones et al. |
| 2009/0192613 A1 | 7/2009 | Wing et al. |
| 2009/0210062 A1 | 8/2009 | Thalgott et al. |
| 2009/0210064 A1 | 8/2009 | Lechmann et al. |
| 2009/0234455 A1 | 9/2009 | Moskowitz et al. |
| 2009/0326580 A1 | 12/2009 | Anderson et al. |
| 2010/0016901 A1 | 1/2010 | Robinson |
| 2010/0125334 A1 | 5/2010 | Krueger |
| 2010/0145459 A1 | 6/2010 | McDonough et al. |
| 2010/0145460 A1 | 6/2010 | McDonough et al. |
| 2011/0118843 A1 | 5/2011 | Mathieu et al. |
| 2011/0295371 A1 | 12/2011 | Moskowitz et al. |
| 2012/0101581 A1 | 4/2012 | Mathieu et al. |
| 2012/0109309 A1 | 5/2012 | Mathieu et al. |
| 2012/0109310 A1 | 5/2012 | Mathieu et al. |
| 2012/0109311 A1 | 5/2012 | Mathieu et al. |
| 2012/0109312 A1 | 5/2012 | Mathieu et al. |
| 2012/0109313 A1 | 5/2012 | Mathieu et al. |
| 2012/0179259 A1 | 7/2012 | McDonough et al. |
| 2013/0073046 A1 | 3/2013 | Zaveloff et al. |
| 2013/0073047 A1 | 3/2013 | Laskowitz et al. |
| 2013/0166032 A1 | 6/2013 | McDonough et al. |
| 2013/0173013 A1 | 7/2013 | Anderson et al. |
| 2013/0268008 A1 | 10/2013 | McDonough et al. |
| 2014/0025168 A1 | 1/2014 | Klimek et al. |
| 2014/0121777 A1 | 5/2014 | Rosen et al. |
| 2014/0180422 A1 | 6/2014 | Klimek et al. |
| 2014/0257487 A1 | 9/2014 | Lawson et al. |
| 2014/0336770 A1 | 11/2014 | Petersheim et al. |
| 2014/0371859 A1 | 12/2014 | Petersheim et al. |

FOREIGN PATENT DOCUMENTS

| | | |
|---|---|---|
| DE | 2821678 A | 11/1979 |
| DE | 3042003 | 7/1982 |
| DE | 3933459 | 4/1991 |
| DE | 4242889 | 6/1994 |
| DE | 4409392 | 9/1995 |
| DE | 4423257 | 1/1996 |
| DE | 19504867 | 2/1996 |
| DE | 29913200 | 9/1999 |
| DE | 202004020209 | 5/2006 |
| EP | 0179695 | 4/1986 |
| EP | 0425542 B1 | 5/1991 |
| EP | 0505634 | 9/1992 |
| EP | 0517030 | 12/1992 |
| EP | 0517030 A3 | 4/1993 |
| EP | 0577178 | 1/1994 |
| EP | 0639351 | 2/1995 |
| EP | 0639351 A3 | 3/1995 |
| EP | 0641547 B1 | 3/1995 |
| EP | 0517030 B1 | 9/1996 |
| EP | 0505634 B1 | 8/1997 |
| EP | 897697 A1 | 2/1999 |
| EP | 0966930 | 12/1999 |
| EP | 0968692 | 1/2000 |
| EP | 0974319 | 1/2000 |
| EP | 0974319 A2 | 1/2000 |
| EP | 1033941 | 9/2000 |
| EP | 1103236 | 5/2001 |
| EP | 0906065 | 1/2004 |
| EP | 1402836 | 3/2004 |
| EP | 1124512 | 9/2004 |
| EP | 1051133 | 10/2004 |
| EP | 1459711 | 7/2007 |
| EP | 1194087 | 8/2008 |
| FR | 2552659 | 4/1985 |

(56) References Cited

FOREIGN PATENT DOCUMENTS

| | | |
|---|---|---|
| FR | 2697996 | 5/1994 |
| FR | 2700947 | 8/1994 |
| FR | 2703580 A1 | 10/1994 |
| FR | 2727003 | 5/1996 |
| FR | 2747034 | 10/1997 |
| FR | 2753368 | 3/1998 |
| GB | 157668 A | 1/1921 |
| GB | 265592 A | 8/1927 |
| GB | 2148122 | 5/1985 |
| GB | 2207607 | 2/1989 |
| GB | 2239482 A | 7/1991 |
| GB | 2266246 A | 10/1993 |
| JP | 03-505416 | 11/1991 |
| JP | 9-280219 | 10/1997 |
| JP | 2006-513752 | 4/2006 |
| RU | 2229271 | 5/2004 |
| RU | 2244527 | 1/2005 |
| RU | 2307625 | 10/2007 |
| SU | 1465040 | 3/1989 |
| WO | WO 88/03417 | 5/1988 |
| WO | WO 88/10100 | 12/1988 |
| WO | WO 89/09035 | 10/1989 |
| WO | WO 90/00037 | 1/1990 |
| WO | WO 92/01428 | 2/1992 |
| WO | WO 92/06005 | 4/1992 |
| WO | WO 93/01771 | 2/1993 |
| WO | WO 95/26164 | 5/1994 |
| WO | WO 95/08964 | 4/1995 |
| WO | WO 95/15133 | 6/1995 |
| WO | WO 95/20370 | 8/1995 |
| WO | WO 95/21053 | 8/1995 |
| WO | WO 96/39988 | 12/1996 |
| WO | WO 96/40015 | 12/1996 |
| WO | WO 97/20526 | 6/1997 |
| WO | WO 97/23175 A | 7/1997 |
| WO | WO 97/25941 | 7/1997 |
| WO | WO 97/25945 | 7/1997 |
| WO | WO 97/37620 | 10/1997 |
| WO | WO 97/39693 | 10/1997 |
| WO | WO 98/17208 | 4/1998 |
| WO | WO 98/17209 | 4/1998 |
| WO | WO 98/55052 | 12/1998 |
| WO | WO 98/56319 | 12/1998 |
| WO | WO 98/56433 | 12/1998 |
| WO | WO 99/09896 | 3/1999 |
| WO | WO 99/09903 | 3/1999 |
| WO | WO 99/27864 | 6/1999 |
| WO | WO 99/29271 | 6/1999 |
| WO | WO 99/32055 | 7/1999 |
| WO | WO 99/38461 | 8/1999 |
| WO | WO 99/38463 | 8/1999 |
| WO | WO 99/56675 | 11/1999 |
| WO | WO 99/63914 | 12/1999 |
| WO | WO 00/07527 | 2/2000 |
| WO | WO 00/07528 | 2/2000 |
| WO | WO 00/25706 | 5/2000 |
| WO | WO 00/30568 | 6/2000 |
| WO | WO 00/40177 | 7/2000 |
| WO | WO 00/41654 | 7/2000 |
| WO | WO 00/59412 | 10/2000 |
| WO | WO 00/66044 | 11/2000 |
| WO | WO 00/66045 | 11/2000 |
| WO | WO 00/74607 | 12/2000 |
| WO | WO 01/08611 | 2/2001 |
| WO | WO 01/56497 | 8/2001 |
| WO | WO 01/62190 | 8/2001 |
| WO | WO 01/80785 | 11/2001 |
| WO | WO 01/56497 A3 | 12/2001 |
| WO | WO 01/93742 | 12/2001 |
| WO | WO 01/95837 | 12/2001 |
| WO | WO 01/56497 B1 | 3/2002 |
| WO | WO 01/93742 A3 | 9/2002 |
| WO | WO 2004/069106 | 8/2004 |
| WO | WO 2005/007040 A | 1/2005 |
| WO | WO 2005/020861 | 3/2005 |
| WO | WO 2006/138500 | 12/2006 |
| WO | WO 2007/098288 | 8/2007 |
| WO | WO 2008/014258 | 1/2008 |
| WO | WO 2008/082473 | 7/2008 |
| WO | WO 2008/124355 | 10/2008 |
| WO | WO 2008/154326 | 12/2008 |
| WO | WO 2009/064644 | 5/2009 |
| WO | WO 2010/054181 | 5/2010 |
| WO | WO 2010/054208 | 5/2010 |
| WO | WO 2012/088238 | 6/2012 |

OTHER PUBLICATIONS

U.S. Appl. No. 11/199,599: Non-Final Office Action dated Apr. 1, 2009, 20 pages.
U.S. Appl. No. 11/199,599: Interview Summary including Draft Claim Amendments dated Sep. 24, 2009, 4 pages.
U.S. Appl. No. 11/199,599: Amendment dated Sep. 29, 2009, 19 pages.
U.S. Appl. No. 11/199,599: Final Rejection dated Dec. 24, 2009, 21 pages.
U.S. Appl. No. 11/199,599: Appeal Brief dated Apr. 15, 2010, 51 pages.
Appendix 1 to Joint Claim Construction Brief; Synthes' Exhibits A-9, in the United States District Court for the District of Delaware Civil Action No. 1:11-cv-00652-LPS, Jun. 8, 2012, 192 pages.
Appendix 2 to Joint Claim Construction Brief; Globus' Exhibits A-F, in the United States District Court for the District of Delaware Civil Action No. 1:11-cv-00652-LPS, Jun. 8, 2012, 146 pages.
Appendix 3 to Joint Claim Construction Brief; Exhibits A-C, in the United States District Court for the District of Delaware Civil Action No. 1:11-cv-00652-LPS, Jun. 8, 2012, 38 pages.
Chadwick et al., "Radiolucent Structural Materials for Medical Applications," www.mddionline.com/print/238, Jun. 1, 2001, accsessed date Jul. 31, 2012, 9 pages.
Expert Report of Dr. Domagoj Carle Regarding the Invalidity of U.S. Patent Nos. 7,846,207, 7,862,616 and 7,875,076, in the United States District Court for the District of Delaware, Civil Action No. 1:11-cv-00652-LPS, Nov. 5, 2012, 149 pages.
Expert Report of John F. Hall, M.D., United States District Court for the District of Delaware, Civil Action No. 1:11-cv-00652-LPS, Dec. 14, 2012, 27 pages.
Expert Report of Paul Ducheyne, Ph.D. Concerning Patent Validity, United States District Court District of Delaware, Civil Action No. 1:11-cv-00652-LPS, Dec. 13, 2012, 155 pages.
Expert Report of Richard J. Gering, Ph.D., CLP In the United States District Court for the District of Delaware, Civil Action No. 1:11-cv-00652-LPS, Dec. 14, 2012, 39 pages.
International Patent Application No. PCT/CH2003/00089, International Search Report dated Dec. 2, 2003, 3 pgs.
International Search Report, completed Aug. 16, 2007 for International Application No. PCT/US2007/005098, filed Feb. 27, 2007.
Joint Claim Construction Brief, in the United States District Court for the District of Delaware, Civil Action No. 1:11-cv-00652-LPS, Jun. 14, 2012, 97 pages.
Jonbergen et al., "Anterior CervicalInterbody fusion with a titanium box cage: Early radiological assessment of fusion and subsidence", The Spine Journal 5, Jul. 2005, 645-649.
Jury Trial Demanded, In the United States District Court for the District of Delaware, Case No. 1:11-cv-00652-LPS, filed Jul. 22, 2011,8 pages.
Jury Verdict Form, United States District Court District of Delaware, Civil Action No. 1:11-cv-00652-LPS, Jun. 14, 2013, 20 pages.
Marcolongo et al., "Trends in Materials for Spine Surgery", Biomaterials and Clinical Use, 6, 2011, 21 pages.
Memorandum Opinion, United States District Court District of Delaware, Civil Action No. 1:11-cv-00652-LPS, May 7, 2013, 33 pages.
Order, United States District Court District of Delaware, Civil Action No. 1:11-cv-00652-LPS, May 15, 2013, 4 pages.
Order, United States District Court District of Delaware, Civil Action No. 1:11-cv-00652-LPS, May 7, 2013, 7 pages.

(56) References Cited

OTHER PUBLICATIONS

Parlov et al., Anterior Lumbar Interbody Fusion with Threaded Fusion Cages and Autologous Grafts, Eur. Spine J., 2000, 9, 224-229.
Plaintiffs' Responses and Objections to Defendant Globus Medical, Inc.'s First Set of Interrogatories (Nos. 1-11), United States District Court for the District of Delaware, Civil Action No. 1:11-cv-00652-LPS, Nov. 14, 2011, 18 pages.
Plaintiffs' Supplemental Responses and Objections to Defendant Globus Medical Inc.'s Interrogatories Nos. 6-10 and Second Supplemental Responses and Objections to Interrogatory No. 5, United States District Court for the District of Delaware, Civil Action No. 11-cv-652-LPS, Sep. 1, 2012, 12 pages.
Redacted version of "Defendant Globus Medical, Inc.'s Answering Brief in Opposition to Plaintiff's Motion for Summary Judgment of No Anticipation by the Kozak and Michelson References", Mar. 12, 2013, 233 pages.
Redacted version of "Opening Brief in Support of Plaintiffs' Motion for Summary Judgment of No Anticipation by the Kozak and Michelson References", United States District Court District of Delaware, Civil Action No. 1:11-cv-00652-LPS, Feb. 13, 2013, 66 pages.
Redacted version of "Plaintiff's Reply Brief in Support of Plaintiff's Motion for Summary Judgment of No Anticipation by the Kozak and Michelson References", Mar. 21, 2013, 11 pages.
Reply Report of Dr. Domagoj Carle Regarding the Invalidity of U.S. Patent Nos. 7,846,207, 7,862,616 and 7,875,076, In the United States District Court for the District of Delaware, Civil Action No. 1:11-cv-00652-LPS, Jan. 4, 2013, 81 pages.
Schleicher et al., "Biomechanical Comparison of Two Different Concepts for Stand alone anterior lumbar interbody fusion", Eur. Spine J., Sep. 2008, 17, 1757-1765.
Scholz et al., "A New Stand-Alone Cervical Anterior Interbody Fusion Device", Spine, Jan. 2009, 34(2), 6 pages.
Second Expert Report of Wilson C. Hayes, Ph.D., United States District Court for the District of Delaware, Civil Action No. 1:11-cv-00652-LPS, Dec. 14, 2012, 22 pages.
Spruit et al., The in Vitro Stabilising Effect of Polyether-etherketone Cages Versus a Titanium Cage of similar design for anterior lumbar interbody fusion, Eur. Spine J., Aug. 2005, 14 752-758.
Trial Transcript, United States District Court District of Delaware, Civil Action No. 1:11-cv00652-LPS, Jun. 10, 2013, 114 pages.
Trial Transcript, United States District Court District of Delaware, Civil Action No. 1:11-cv00652-LPS, Jun. 11, 2013, 98 pages.
Trial Transcript, United States District Court District of Delaware, Civil Action No. 1:11-cv00652-LPS, Jun. 12, 2013, 75 pages.
Trial Transcript, United States District Court District of Delaware, Civil Action No. 1:11-cv00652-LPS, Jun. 13, 2013, 94 pages.
Trial Transcript, United States District Court District of Delaware, Civil Action No. 1:11-cv00652-LPS, Jun. 14, 2013, 26 pages.
Trial Transcript, United States District Court District of Delaware, Civil Action No. 1:11-cv00652-LPS, Jun. 3, 2013, 98 pages.
Trial Transcript, United States District Court District of Delaware, Civil Action No. 1:11-cv00652-LPS, Jun. 4, 2013, 110 pages.
Trial Transcript, United States District Court District of Delaware, Civil Action No. 1:11-cv00652-LPS, Jun. 5, 2013, 99 pages.
Trial Transcript, United States District Court District of Delaware, Civil Action No. 1:11-cv00652-LPS, Jun. 6, 2013, 80 pages.
Trial Transcript, United States District Court District of Delaware, Civil Action No. 1:11-cv00652-LPS, Jun. 7, 2013, 97 pages.
U.S. Appl. No. 60/988,661, Nov. 16, 2007, Kueenzi et al.
U.S. Appl. No. 61/535,726, Sep. 16, 2011, Zaveloff.
Japanese Patent Application No. 2011-534926: Office Action dated Oct. 30, 2013, 7 pages.
Japanese Patent Application No. 2011-534928: Office Action dated Sep. 30, 2013, 11 pages.
Russian Patent Application No. 2011-1122797: Decision to Grant dated Oct. 9, 2013, 20 pages.

Synthes Spine, "SynFix-LR System. Instruments and Implants for Stand-Alone Anterior Lumbar Interbody Fusion (ALIF)", Technique Guide dated 2008, pp. 2-40, Published by Synthes Spine (USA).
Synthes Spine, "Zero-P Instruments and Implants. Zero-Profile Anterior Cervical Interbody Fusion (ACIF) device", Technique Guide dated 2008, pp. 2-32, Published by Synthes Spine (USA).
Bray, "InterPlate Spine Fusion Device: Subsidence Control Without Stress Shielding", Orthopaedic Product News, Sep./Oct. 2006, pp. 22-25.
International Search Report, Mailed Mar. 20, 2009, for PCT International Application No. PCT/US08/82473, filed Nov. 5, 2008.
Written Opinion, Mailed Mar. 20, 2009, for PCT International Application No. PCT/US08/82473, filed Nov. 5, 2008.
Synthes Spine, "CorticoCancellous ACF Spacer. An allograft space or anterior fusion of the cervical spine," brochure, Musculoskeletal Transplant Foundationm, 2003, 6 pages.
International Patent Application PCT/US2011/066421, International Search Report dated Jun. 14, 2012, 31 pages.
U.S. Appl. No. 60/068,205, Dec. 19, 1997, Urbahns.
U.S. Appl. No. 60/071,527, Jan. 15, 1998, Urbahns.
Synthes History and Evolution of LBIF Brochure; Nov. 2015, 30 pages.
Synthes Spine Cervical Stand-Alone Devices Presentation Brochure; 2010, 40 pages.
DePuy Motech Surgical Titanium Mesh Brochure; 1998, 13 pages.
AcroMed Carbon Fiber interbody Fusion Devices; Jan. 1998, 8 pages.
Carbon Fiber Composite Ramps for Lumbar Interbody Fusion; Apr. 1997, 2 pages.
Al-Sanabani, Application of Calcium Phosphate Materials in Dentistry, vol. 2013, Int. J. Biomaterials, 1-12, 2013.
Bailey, Stabilzation of the Cervical Spine by Anterior Fusion, 42-A(4), J. Bone Joint Surg., 565-594, Jun. 1960.
Banward, Iliac Crest Bone Graft Harvest Donor Site Morbidity, 20 (9) Spine 1055-1060, May 1995.
Benezech, L'arthrodese Cervicale Par Voie Anterieure a L'Aide de Plaque-Cage P.C.B., 9(1) Rachis 1, 47, 1997 (w/Translation).
Brantigan I/F Cage for PLIF Surgical Technique Guide; Apr. 1991, 22 pages.
Brantigan, A Carbon Fiber Implant to Aid Interbody Lumbar Fusion, 16(6S) Spine S277-S282, Jul. 1991.
Brantigan, Compression Strength of Donor Bone for Posterior Lumbar Interbody Fusion, 18(9) Spine 1213-1221, 1993.
Brantigan, Interbody Lumbar Fusion Using a Carbon Fiber Cage Implant Versus Allograft Bone, 19(13) Spine 1436-1444, 1994.
Brantigan, Intervertebral Fusion, Chapter 27, Posterior Lumbar Interbody Fusion Using the Lumbar Interbody Fusion Cage, 437-466, 2006.
Brantigan, Pseudarthrosis Rate After Allograft Posterior Lumbar Interbody Fusion with Pedicle Screw and Plate Fixation, 19(11) Spine 1271-1280, Jun. 1994.
Cloward, Gas-Sterilized Cadaver Bone Grafts for Spinal Fusion Operations, 5(1) Spine 4-10 Jan./Feb. 1980.
Cloward, The Anterior Approach for Removal of Ruptured Cervical Disks, vol. 15, J. Neuro. 602-617, 1958.
Delecrin, Morbidite du Prelevement de Greffons osseuz au Niveau des Cretes Iliaques dans la Chirurgie Du Rachis; Justification du recours aux substituts osseuz, 13(3) Rachis 167-174, 2001 (w/Translation).
Dereymaeker, Nouvelle Cure neuro-Chirurgicale de discopathies Cervicales, 2 Neurochirurgie 226-234; 1956 (w/Translation).
Dickman, Internal Fixation and Fusion of the Lumbar Spine Using Threaded Interbody Cages, 13(3) Barrow Quarterly (1997); http://www.thebarrow.org/Education_And_Resources/Barrow_Quarterly/204837.
Enker, Interbody Fusion and Instrumentation, No. 300 Clin. Orth. Rel. Res. 90-101, Mar. 1994.
Fassio, Use of Cervical Plate-Cage PCB and Results for Anterior Fusion in Cervical Disk Syndrome, 15(6) Rachis 355-361, Dec. 2003 Translation.
Fowler, Complications Associated with Harvesting Autogenous Iliac Bone Graft, 24(12) Am. J. Ortho. 895-904, Dec. 1995.

(56) References Cited

OTHER PUBLICATIONS

Fuentes, Les Complications de la Chirurgie Par Voie Anterieure du Rachis Cervical, 8(1) Rachis 3-14, 1996 (w/Translation).
Germay, Resultats Cliniques de Ceramiques D'hydroxyapatite dans les arthrodeses Inter-somatiques du Rachis Cervical Par Voie Anterieure. Etude Retrospective a Propose de 67 cas. 13(3), Rachis 189-195, 2001 (w/Translation).
Graham, Lateral Extracavitary Approach to the Thoracic and Thoracolumbar Spine, 20(7) Orthopedics, 605-610, Jul. 1997.
Gunatillake, Biodegradable Synthetic Polymers for Tissue Engineering, vol. 5, Eur. Cells Materials, 1-16, 2003.
Huttner, Spinal Stenosis & Posterior Lumbar Interbody Fusion, No. 193, Clinical Ortho Rel. Res. 103-114, Mar. 1985.
Jost, Compressive Strength of Interbody Cages in the Lumbar Spine: the Effect of Cage Shape, Posterior Instrumentation and Bone Density, 7 Eur. Spine J. 132-141, 1998.
Kastner, Advanced X-Ray Tomographic Methods for Quantitative Charecterisation of Carbon Fibre Reinforced Polymers, 4th Annual Intern. Symposium on NDT in Aerospace, 2012, 9 pages.
Khan, Chapter 2—Implantable Medical Devices, Focal Controlled Drug Delivery, Advances in Delivery Science and Technology, A.J. Domb and W. Khan (eds.) 2014.
Kozak, Anterior Lumbar Fusion Options, No. 300, Clin. Orth. Rel. Res., 45-51, 1994.
Kroppenstedt, Radiological Comparison of Instrumented Posterior Lumbar Interbody Fusion with One or Two Closed-Box Plasmapore Coated Titanium Cages, 33(19) Spine, 2083-2088, Sep. 2008.
Lund, Interbody Cage Stabilisation in the Lumbar Spine, 80-B(2) J Bone Joint Surg., 351-359, Mar. 1998.
Lyu, Degradability of Polymers for Implantable Biomedical Devices, 10, Int. J. Mol. Sci., 4033-4065, 2009.
Malca, Cervical Interbody Xenograft with Plate Fixation, 21(6) Spine, 685-690, Mar. 1996.
McAfee, Minimally Invasive Anterior Retroperitoneal Approach to the Lumbar Spine, 21(13) Spine, 1476-1484, 1998.
Nasca, Newer Lumbar Interbody Fusion Techniques, 22(2) J. Surg. Ortho. Advances, 113-117, 2013.

PCB Evolution Surgical Technique Guide 2010.
Polysciences Inc. Info Sheet 2012.
Porex Website, http://www.porex.com/technologies/materials/porous-plastics, Porous Plastic Materials, accessed Aug. 21, 2015, 2 pages.
Samandouras, A New Anterior Cervical Instrumentation System Combining an Intradiscal Cage with an Integrated Plate, 26(10) Spine, 1188-1192, 2001.
Sonntag, Controversy in Spine Care, Is Fusion Necessary After Anterior Cervical Discectomy 21(9) Spine, 1111-1113, May 1996.
Tamariz, Biodegradation of Medical Purpose Polymeric Materials and Their Impact on Biocompatibility, Chapter 1, Intech-bio degradation Life of Science, 2013; 28 pages.
Tan, A Modified Technique of Anterior Lumbar Fusion with Femoral Cortical Allograft, 5(3) J. Ortho. Surg. Tech., 83-93, 1990.
Verbiest H., La Chirurgie Anterieure et Laterale du Rachis Cervical, 16(S2) Neurochirurgie 1- 212; 1970 (w/Translation).
Wang, Increased Fusion Rates with Cervical Plating for Two-Level Anterior Cervical . Discectomy and Fusion, 25(1) Spine 41-45, Jan. 2000.
Watters, Anterior Cervical Discectomy with and without Fusion, 19(20) Spine 2343-2347 Oct. 1994.
Weiner, Spinde Update Lumbar Interbody Cages, 23(5) Spine, 634-640, Mar. 1998.
White, Relief of Pain by Anterior Cervical-Spine Fusion for Spondylosis, 55-A(3) J. Bone Joint Surg. 525-534, Apr. 1973.
Whitesides, Lateral Approach to the Upper Cervical Spine for Anterior Fusion, vol. 59, South Med J, 879-883, Aug. 1966.
Wilson, Anterior Cervical Discectomy without Bone Graft, 47(4) J. Neurosurg. 551-555, Oct. 1977.
Younger, Morbidity at Bone Graft Donor Sites, 3(3) J. Orth. Trauma, 192-195, 1989.
Dabrowski, Highly Porous Titanium Scaffolds for Orthopaedic Applications, J. Biomed Mater. Res. B. Appl. Biomat. Oct. ;95(1):53-61, 2010.
Takahama, A New Improved Biodegradable Tracheal Prosthesis Using Hydroxy Apatite and Carbon Fiber 35(3) ASAIO Trans, 291-293, Jul.-Sep. 1989.
Wang, Determination of Cortical Bone Porosity and Pore Size Distribution using a Low Field Pulsed NMR Approach, J. Orthop Res., Mar.; 21(2):312-9 Mar. 2003.

INTERVERTEBRAL IMPLANT

CROSS REFERENCE TO RELATED APPLICATIONS

This application is a continuation of U.S. patent application Ser. No. 13/012,626, filed Jan. 24, 2011, which is a continuation of U.S. patent application Ser. No. 12/574,222, filed Oct. 6, 2009, now U.S. Pat. No. 7,875,076, which is a continuation of U.S. patent application Ser. No. 11/751,757, filed May 22, 2007, now U.S. Pat. No. 7,618,456, which is a continuation of U.S. patent application Ser. No. 10/923,534, filed Aug. 19, 2004, now U.S. Pat. No. 7,232,464, which is a continuation of International Application No. PCT/CH02/00099, filed Feb. 19, 2002. The entire contents of each of the applications identified above are expressly incorporated herein by reference thereto.

TECHNICAL FIELD

The present invention relates to an intervertebral implant.

BACKGROUND

Such an intervertebral implant is known from the British patent document 2,207,607 A which discloses a horseshoe implant structure having a plurality of cylindrical holes. These holes are fitted with inner, smooth surfaces and comprise only one stop for the heads of the bone screws to be inserted into them. This design incurs the drawback that the inserted affixation screws may be anchored into the bone only by their shanks, a rigid connection with the horseshoe shaped intervertebral implant being lacking. As soon as the anchoring of the bone screw in the bone is weakened, the intervertebral implant becomes displaceable relative to the screw and the bone screws may then migrate while endangering the blood vessels. Moreover the loosening of the intervertebral implant may entail pseudoarthrosis.

The above cited state of the art is intended merely to elucidate the background of the present invention but it does imply that the cited state of the art had actually been made public or was publicly known at the time of this application or at the time of its priority.

SUMMARY

The objective of the present invention is palliation. This invention creates an intervertebral implant which is able to rigidly connect to bone affixation means in a manner that even in the event of bone structure weakening, loosening between the intervertebral implant and the bone affixation means shall be precluded.

The above problem is solved in the present invention by an intervertebral implant exhibiting the features of claim 1.

The advantages offered by the present invention substantially are attained by the rigid, that is by the firm connection between the intervertebral implant and the longitudinal affixing elements. Basically two different embodiment modes are available to attain said rigid connection.

In a first embodiment mode, at least one of the boreholes shall be internally threaded. In this case a matching bone screw fitted with a thread head may be rigidly screwed into the implant.

As regards a second embodiment mode, a front plate is mounted at the front surface of the three dimensional (3D) implant structure so as to be configured vertically to the horizontal center plane of the intervertebral implant, said boreholes passing through said front plate and receiving the anchored longitudinal affixation elements. Compared to the state of the art of a two-part implant, wherein a front plate is implanted in a separate operational step, the above design of the present invention offers the advantage that the intervertebral implant shall be implanted in a single step and hence in a simple and quicker manner. The invention offers a further advantage in that the intervertebral implant shall be affixed as frontally to the vertebra as possible, namely at a place where good bone material may be expected to be. As a result anterior displacement is restricted without thereby incurring greater danger to the surrounding structures than when using a state of the art intervertebral implant. The load still is being borne by the compressed vertebral implant, not by the front plate or the affixation screws.

In yet another embodiment mode of the present invention, the front plate is displaceably configured in the 3D implant structure in order that it may move vertically relative to this 3D implant structure. "Stress shielding" is attained in this manner (namely protection from or neutralization of mechanical stresses), and as a result the end plates may gradually match the intervertebral implant during the healing process.

As regards a further embodiment, the front plate is made of a material different from that of the 3D implant structure.

As regards a further embodiment of the present invention, at least one borehole tapers conically towards its underside and as a result a bone screw fitted with a matching conical head may be rigidly anchored in said borehole. Preferably the conical borehole exhibits a cone angle smaller than the resultant angle of friction. Appropriately the borehole's conicity shall be 1:3.75 to 1:20, preferably 1:5 to 1:15.

As regards a further embodiment mode of the present invention, the intervertebral implant side faces shall all be substantially convex.

Appropriately the intervertebral implant's top and/or undersides are not planar but convex. In this manner better matching to the end plates of the adjacent vertebras may be attained.

The boreholes preferably shall not pass through the left and right intervertebral implant side faces. Preferably again no borehole shall run through the front surface.

As regards a further preferred embodiment mode of the present invention, at least two boreholes shall be mutually parallel. This features facilitates inserting the vertebral implant during implantation.

As regards another preferred embodiment mode of the present invention, at least two boreholes shall run in mutually divergent manner as seen from the front side. As a result the bone screws shall move into a vertebral region offering better bone quality than found at the vertebra's center. Appropriately the borehole axes subtend an angle of 25 degrees to 70 degrees, preferably 35 degrees to 55 degrees with the horizontal center plane. This feature offers improved access for screw insertion.

As regards a further embodiment mode of the present invention, the boreholes shall not cross the horizontal center plane.

Depending on circumstance, two, three, four or even more longitudinal affixation elements may rigidly connected to the intervertebral implant; appropriately at least one affixation element shall pass through the top side and at least one affixation element shall pass through the intervertebral implant side.

Preferably the longitudinal affixation elements shall be bone screws comprising a head and a shank, said head preferably being fitted with an external thread that matches the inner thread of the intervertebral implant's borehole. As regards a second appropriate connection, preferably a bone screw shall be used of which the head tapers conically in the direction of the shank, the head's conicity corresponding to that of the intervertebral implant's borehole.

Regarding a further embodiment mode, at least two longitudinal affixation elements pass through the top side and at least two longitudinal affixation elements pass through the underside. In this manner the intervertebral implant is optimally anchored into the adjacent vertebras.

Preferably the screw-shaped longitudinal affixation elements exhibit a self-boring and self tapping external thread. The longitudinal affixation elements also may be designed as unthreaded cylindrical pins fitted with a boring tip, preferably in the form of a trocar.

In another embodiment variation, the longitudinal affixation elements are spiral springs; lastly said longitudinal affixation elements also may be designed as single or multi-wing spiral blades.

In a further embodiment mode of the present invention, the longitudinal affixation element tip may be anchored in the structure of the intervertebral implant, as a result of which the head of the longitudinal affixation element may be anchored in the adjacent vertebra.

In a further embodiment mode of the present invention, the longitudinal affixation element head exhibits a widened diameter; also a support disk is provided for said head to rest against the vertebra.

The intervertebral implant may be made of any physiologically compatible material, though appropriately the implant structure shall consist of a physiologically compatible plastic, preferably an unreinforced plastic. The advantage offered by the invention over the already known, fiber-reinforced plastics used in implantology is that no reinforcing fibers will be bared—an eventuality that would be clinically disadvantageous. Appropriately bone screws consisting of non-reinforced plastic of which the external threads exhibit load bevels of 11 degrees to 14 degrees, preferably 12 degrees to 13 degrees, may be used in such an implant structure. The relatively small slope of the load bevel implements high clamping forces, as a result of which radial elongation and danger of cracking of the plastic are reduced. Appropriately the bone screws' external thread exhibits the bones at an angular pitch of 6 degrees to 10 degrees, preferably 7 degrees to 9 degrees. This particular angular pitch produces thread self-locking and prevents the bone screw from loosening on its own.

The borehole may be in the form of a metal bush fitted with an inner thread for the purpose of improving anchoring the bone screw in the plastic implant structure. The intervertebral implant also may consist partly of plastic and, in the borehole zones, of metal. This design offers improved guidance and anchoring of the bone screw in the intervertebral implant.

As regards a further preferred embodiment mode, the inside borehole walls are smooth, the thread head of a metallic, longitudinal affixation element cutting or tapping into said smooth wall.

BRIEF DESCRIPTION OF THE DRAWINGS

The present invention and further embodiment modes of it are elucidated below in relation to the partly schematic representation of two illustrative embodiments.

DETAILED DESCRIPTION OF ILLUSTRATIVE EMBODIMENTS

Figure 1:
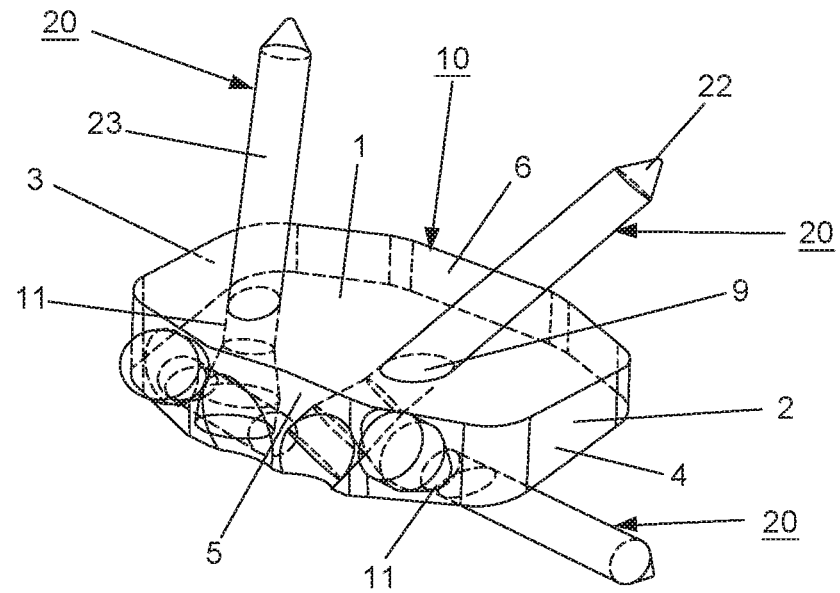
FIG. 1 is a perspective view including a partial section of the intervertebral implant with inserted bone screws.
Figure 2:
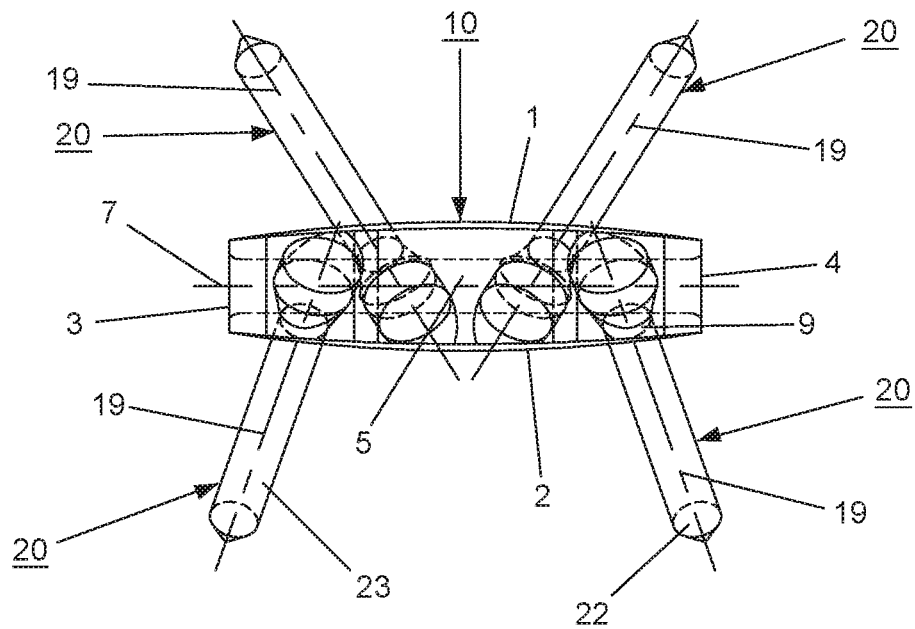
FIG. 2 is a front view of the intervertebral implant of FIG. 1.
Figure 3:
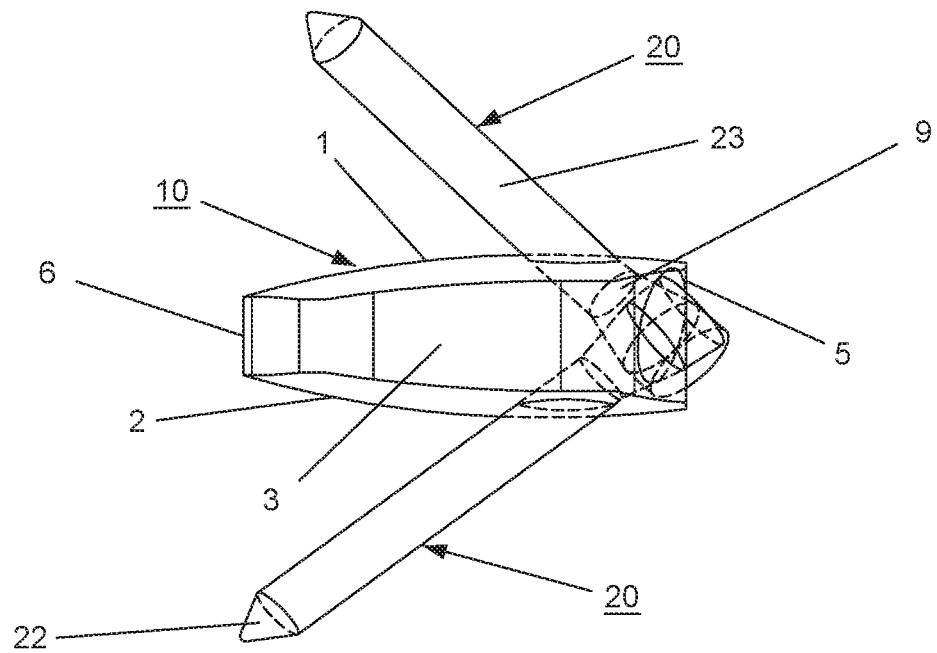
FIG. 3 is a side view of the intervertebral implant of FIG. 1.
Figure 4:
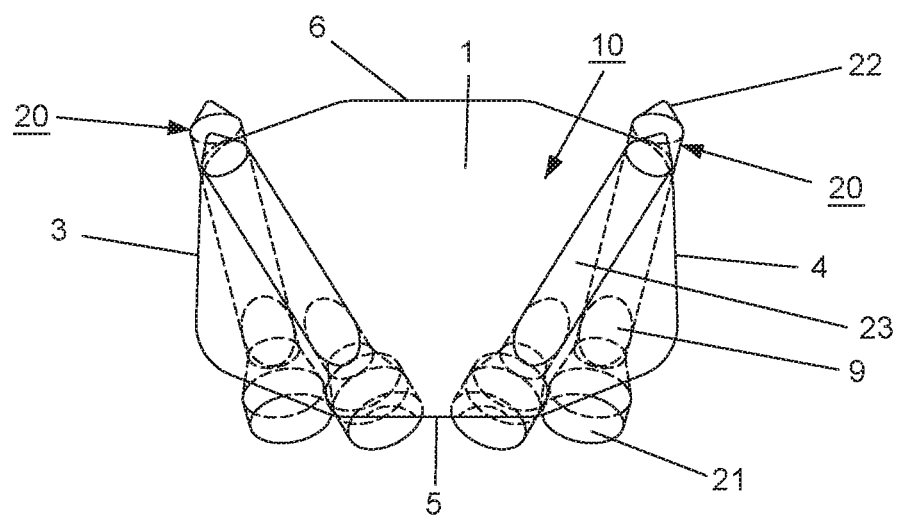
FIG. 4 is a top view of the intervertebral implant of FIG. 1.

The intervertebral implant of FIGS. 1 through 4 consists of a 3D structure 10 exhibiting both a convex top side 1 and a convex underside 2, the two sides each being designed to rest against the end plates of two adjacent vertebras. To attain improved anchoring, the top side 1 and the underside 2 may be topographically shaped and be fitted with grooves, ribs or teeth, or their surfaces may be merely roughened.

The 3D implant structure 10 moreover comprises a left side face 3 and a right side face 4, also a front face 5 and a rear face 6. The implant structure 10 also may be hollow and its outer surface may comprise perforations.

The implant structure 10 comprises a plurality of boreholes 9 passing through it and receiving longitudinal affixation elements 20. Preferably four such boreholes 9 shall be provided.

At least one of the boreholes 9 is designed in a way that the longitudinal affixation element 20 received therein may be rigidly connected to the intervertebral implant. The boreholes 9 are conical for that purpose.

Preferably the affixation elements 20 are bone screws having a head 21 and a tip 22. The head 21 conically tapers toward the shank 23, the conicity of the head 21 corresponding to the conicity of the borehole 9. Moreover the four boreholes 9 may be fitted with inner threads 11.

Figure 5:
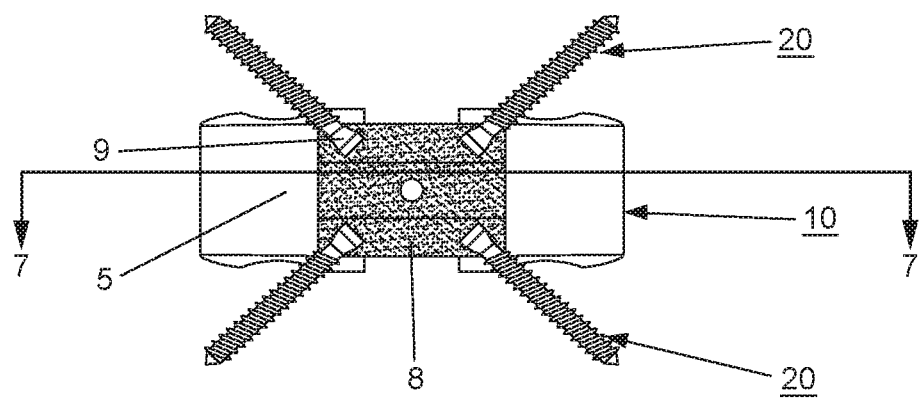
FIG. 5 is a front view of the intervertebral implant with a front insert, in partial section.
Figure 6:
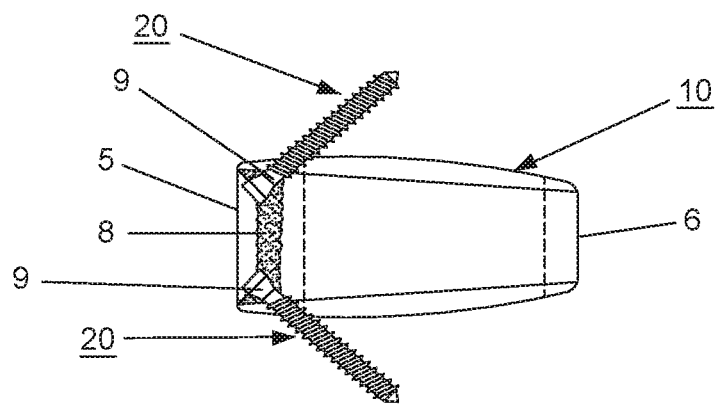
FIG. 6 is a vertical, longitudinal section of the intervertebral implant of FIG. 5.
Figure 7:
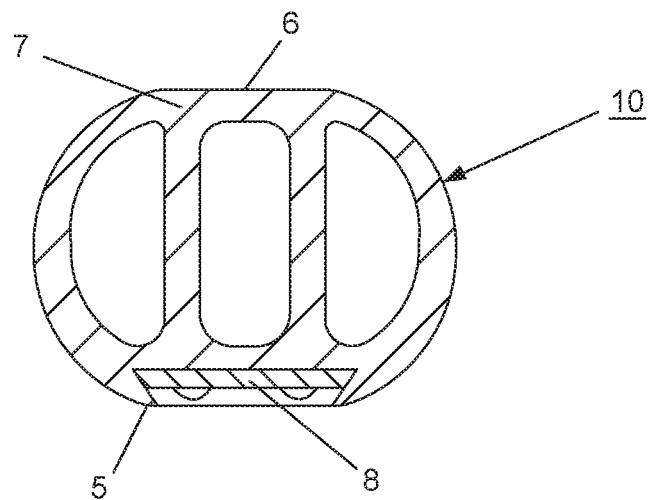
FIG. 7 is a horizontal cross-section of the intervertebral implant of FIG. 5.

As regards the embodiment variation shown in FIGS. 5 through 7, the 3D structure 10 is fitted at its front face 5 with a preferably metallic insert 8 into which the affixation elements 20 may be anchored. The insert 8 is mounted in vertically displaceable manner in the 3D structure 10.

While the invention has been shown and described herein with reference to particular embodiments, it is to be understood that the various additions, substitutions, or modifications of form, structure, arrangement, proportions, materials, and components and otherwise, used in the practice and which are particularly adapted to specific environments and operative requirements, may be made to the described embodiments without departing from the spirit and scope of the present invention. Accordingly, it should be understood that the embodiments disclosed herein are merely illustrative of the principles of the invention. Various other modifications may be made by those skilled in the art which will embody the principles of the invention and fall within the spirit and the scope thereof.

What is claimed:

1. An intervertebral implant configured to be inserted into a space between an endplate of an upper vertebral body and an endplate of a lower vertebral body, the intervertebral implant comprising:

an implant structure defining a front face, a rear face opposite the front face in a first direction, a top side, an underside opposite the top side in a second direction that is perpendicular to the first direction, the implant structure defining a height measured from the top side to the underside in the second direction, the implant structure further defining an opening that extends along the second direction from the top side to the underside, the front face including a front face front-most location such that the implant structure is devoid of a location offset from the front face front-most location in a direction opposite the first direction, the rear face including an implant structure rear-most location such that the implant structure is devoid of a location offset from the implant structure rear-most location in the first direction; and a plate including a front plate surface and a rear plate surface that is opposite the front plate surface, the plate configured to be received by the implant structure such that 1) the rear plate surface faces the implant structure and 2) a portion of the plate is positioned between the front face front-most location and the implant structure rear-most location with respect to the first direction, the plate further including an upper plate surface and a lower plate surface opposite the upper plate surface, the plate defining a first hole that is configured to receive a portion of a first affixation element such that the first affixation element is inserted through the endplate of the upper vertebral body, the plate defining a second hole that is: 1) nonparallel with the first hole, and 2) configured to receive a portion of a second affixation element such that the second affixation element is configured to be inserted into the lower vertebral body, wherein when the plate is mounted to the implant structure: 1) a portion of the plate that defines a lower edge of an exit of the first hole through the front plate surface is aligned with the rear face with respect to the first direction, 2) the first hole positioned such that an entirety of the exit of the first hole is between the top side and the underside with respect to the second direction, 3) the lower edge of the exit is closer to the underside than any other portion of the exit, 4) the intervertebral implant defines an intervertebral implant rear-most location such that the intervertebral implant is devoid of a location offset from the intervertebral implant rear-most location in the first direction, and 5) the rear face of the implant structure includes the intervertebral implant rear-most location.

2. The intervertebral implant of claim 1, wherein the front plate surface defines uppermost and lowermost ends that are configured to be disposed in the space when the plate is mounted to the front face.

3. The intervertebral implant of claim 1, further comprising the first affixation element configured to be inserted through the first hole, and into the endplate of the upper vertebral body, to anchor the intervertebral implant to the upper vertebral body.

4. The intervertebral implant of claim 3, wherein the second hole is positioned such that an entirety of the second hole exits the through the front plate surface between the top side and the underside with respect to the second direction.

5. The intervertebral implant of claim 4, wherein the affixation element is a first affixation element, the intervertebral implant further comprising a second affixation element configured to be inserted through the second hole, and into the endplate of the lower vertebral body, to anchor the intervertebral implant to the lower vertebral body.

6. The intervertebral implant of claim 1, wherein the plate is configured to be mounted to the implant structure such that the rear plate surface abuts the front face of the implant structure.

7. The intervertebral implant of claim 1, wherein the implant structure rear-most location is offset from the front face front-most location a maximum distance with respect to the first direction.

8. The intervertebral implant of claim 7, wherein the plate defines a maximum thickness measured from the front plate surface to the rear plate surface in the first direction, and the maximum distance is greater than the maximum thickness.

9. The intervertebral implant of claim 1, wherein when the plate is mounted to the implant structure the intervertebral implant defines a central axis that extends along the first direction and is aligned with the rear face along the first direction, and the central axis is positioned equidistant from both the top side and the underside with respect to the second direction.

* * * * *